United States Patent
Abekawa et al.

(10) Patent No.: US 7,999,125 B2
(45) Date of Patent: Aug. 16, 2011

(54) METHOD FOR PRODUCING PROPYLENE OXIDE

(75) Inventors: Hiroaki Abekawa, Toyonaka (JP); Tomonori Kawabata, Toyonaka (JP); Makoto Yako, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/665,172

(22) PCT Filed: Jun. 19, 2008

(86) PCT No.: PCT/JP2008/061592
§ 371 (c)(1),
(2), (4) Date: Dec. 17, 2009

(87) PCT Pub. No.: WO2008/156205
PCT Pub. Date: Dec. 24, 2008

(65) Prior Publication Data
US 2010/0197945 A1    Aug. 5, 2010

(30) Foreign Application Priority Data
Jun. 21, 2007    (JP) ................................ 2007-163646

(51) Int. Cl.
*C07D 301/12* (2006.01)
*C07D 301/06* (2006.01)
(52) U.S. Cl. ..................... 549/533; 549/531; 549/532
(58) Field of Classification Search .................. 549/531, 549/533, 532
See application file for complete search history.

(56) References Cited

U.S. PATENT DOCUMENTS

| | | |
|---|---|---|
| 4,131,646 A | 12/1978 | Gosser |
| 5,214,168 A | 5/1993 | Zajacek et al. |
| 6,005,123 A | 12/1999 | Dessau et al. |
| 6,008,388 A | 12/1999 | Dessau et al. |
| 2009/0054670 A1 | 2/2009 | Kawabata et al. |
| 2009/0209772 A1 | 8/2009 | Kawabata et al. |

FOREIGN PATENT DOCUMENTS

| | | |
|---|---|---|
| EP | 0 568 337 | 11/1993 |
| JP | 04-352771 | 12/1992 |
| WO | WO 99/52884 | 10/1999 |
| WO | WO 2007/080995 | 7/2007 |

OTHER PUBLICATIONS

"Next Generation and Non-Halogen Chemical Process Technology Development Result Report 2002," *New Energy and Industrial Technology Development Organization* (the consignment ahead: Japan Chemical Innovation Institute), pp. 152-180 with translated excerpts (pp. 1-32).

*Primary Examiner* — Taylor Victor Oh
(74) *Attorney, Agent, or Firm* — Foley & Lardner LLP

(57) ABSTRACT

There is disclosed a method for producing propylene oxide, which includes: reacting propylene, oxygen, and hydrogen in the presence of a noble metal catalyst and a titanosilicate catalyst in a liquid phase containing a polycyclic compound, which is unsubstituted or substituted with at least one substituent selected from Group B below, wherein the polycyclic compound is composed of two or more identical or different ring compounds selected from Group A below and the ring compounds are fused, directly bonded, or bonded by a linkage group selected from the group consisting of an oxygen atom, carbon chain, and a group composed of oxygen atom(s) and a carbon chain, provided that said polycyclic compound is not a polycyclic compound having hydroxy groups or oxo groups at para or. ortho positions. Group A consisting of benzene, cyclopentadiene, cycloheptatriene, furane, pyrane, cyclopentene, cyclopentane, cyclohexane, cyclohexene, cyclohexadiene, cycloheptane, cycloheptene, and cycloheptadiene. Group B consisting of halogen atom, alkyl group, alkenyl group, alkoxy group, hydroxyalkyl group, acyl group, oxo group, hydroxy group, and cyano group.

10 Claims, No Drawings

METHOD FOR PRODUCING PROPYLENE OXIDE

TECHNICAL FIELD

The present invention relates to a method for producing propylene oxide from propylene, oxygen, and hydrogen.

BACKGROUND ART

It has been known that, in the production of propylene oxide from propylene, oxygen, and hydrogen with use of a noble metal catalyst and a crystalline titanosilicate catalyst, the use of a palladium catalyst and a TS-I catalyst in combination with a phosphorus modifier, a sulfur modifier or the like reduces an amount of a propane byproduct (See, for example, Japanese Translation of PCT International Application, No. 511454/2002 (Tokuhyou 2002-51 1454), which is an equivalent of WO99/52884). The addition of a phosphorus modifier, however, involves use of an organic phosphorus compound, which has a negative influence on the environment. Further, there is another disadvantage in that the addition of a sulfur modifier reduces the production amount of propylene oxide. Another known method for producing propylene oxide involves use of palladium and a Ti-MWW catalyst in combination with water and acetonitrile as a solvent (See Heisei 14 *nendo Jisedai Kagaku Process Gijutu Kaihatu Non-halogen Kagaku Process Gijutu Kaihatu Seiko Houkokusho* (Report of R&D projects for Technology of Next-generation Chemical Process/Technology for Non-halogen Chemical Process, FY2002 Annual Report), pp. 152-180,(2003)).). Unfortunately, the above methods for producing propylene oxide are not sufficiently efficient.

DISCLOSURE OF INVENTION

In view of the aforementioned problem, an object of the present invention is to provide a method for more efficiently producing propylene oxide from propylene, oxygen, and hydrogen with use of a noble metal catalyst and a titanosilicate catalyst.

A method of the present invention is for producing propylene oxide, which includes: reacting propylene, oxygen, and hydrogen in the presence of a noble metal catalyst and a titanosilicate catalyst in a liquid phase containing a polycyclic compound, which is unsubstituted or substituted with at least one substituent selected from Group B below, wherein the polycyclic compound is composed of two or more identical or different ring compounds selected from Group A below and the ring compounds are fused, directly bonded, or bonded by a linkage group selected from the group consisting of an oxygen atom, carbon chain, and a group composed of oxygen atom(s) and a carbon chain, provided that said polycyclic compound is not a polycyclic compound having hydroxy groups or oxo groups at para or ortho positions.

Group A consisting of benzene, cyclopentadiene, cycloheptatriene, furane, pyrane, cyclopentene, cyclopentane, cyclohexane, cyclohexene, cyclohexadiene, cycloheptane, cycloheptene, and cycloheptadiene.

Group B consisting of halogen atom, alkyl group, alkenyl group, alkoxy group, hydroxyalkyl group, acyl group, oxo group, hydroxy group, and cyano group.

The present invention enables efficient production of propylene oxide from propylene, oxygen, and hydrogen.

For a fuller understanding of the nature and advantages of the invention, reference should be made to the ensuing detailed description.

BEST MODE FOR CARRYING OUT THE INVENTION

Examples of condensation of cyclic compounds in Group A, which compounds form a polycyclic compound for use in the present invention, encompass ortho-condensation, spiro-condensation, and bridge condensation. Examples of the linkage groups that bond rings of cyclic compounds in Group A encompass: ether-bonded oxygen (—O—); a carbon chain (e.g. a methine group, an alkylene group such as a methylene group, a dimethylene group, or a trimethylene group); and a group containing an oxygen atom and a carbon chain (e.g. a keto group (—(CO)—), and —OCH$_2$—). The above polycyclic compound is typically composed of 2 to 30 rings (e.g. carbocycles), preferably 2 to 4 rings. Examples of the polycyclic compound composed of fused cyclic compounds selected from Group A encompass a polycyclic compound composed of fused hydrocarbon rings, which are, for example, (i) a compound in which two rings are fused, e.g. pentalene, naphthalene, heptalene, indane, indene, azulene, or the like, (ii) a compound in which three rings are fused, e.g. anthracene, phenanthrene, phenalene, dihydroanthracene, indacene, fluorene, and dibenzosuberane, (iii) a compound in which four rings are fused, e.g. tetracene, pyrene, triphenylene, chrysene, tetraphene, fluoracene, and 1H-cyclopenta[a]phenanthrene, (iv) a compound in which five rings are fused, e.g. dibenzo[c,g]phenanthrene, pentacene, and benzo[pqr]tetraphene, (v) a compound in which six rings are fused, e.g. hexaphene and helicene, and (vi) a compound in which 12 rings are fused cyclically, e.g. kekulene. Examples of the polycyclic compound substituted with at least one substituent selected from Group B encompass polycyclic compounds, which are composed of each polycyclic compound as exemplified above and at least one substituent selected from Group B.

Examples of anthracene substituted with a substituent selected from Group B encompass, for example, 9-acetylanthracene, anthracene-9-methanol, 9-bromoanthracene, 2-(t-butyl)anthracene, 9,10-diethoxyanthracene, 9,10-dimethylanthracene, 9,10-dinitroanthracene, 9-methylanthracene, and 9-vinylanthracene.

Examples of dihydroanthracene substituted with at least one substituent selected from Group B encompass anthrone, which is dihydroanthracene substituted with an oxo group.

Examples of the polycyclic compound in which rings are spiro-fused encompass 1H,1'H-2,2'-spirobi[naphthalene] and 1,1'-spirobi[indene].

Examples of the polycyclic compound in which rings are fused and bridged encompass dicyclopentadiene, 2-norbornene, and adamantane.

Examples of the polycyclic compound in which rings are fused directly via a single bond encompass biphenyl, cyclohexylbenzene, 1-phenyl-1-cyclohexene, 1,4-dicyclohexylbenzene, and the like.

Examples of the polycyclic compound in which rings are bonded with each other via the above linkage group encompass (i) a polycyclic compound in which rings are bonded with each other via a carbon chain such as diphenylmethane, bibenzyl, triphenylmethane, and tetraphenylmethane, and (ii) a polycyclic compound in which rings are bonded with each other via ether oxygen such as diphenyl ether.

Examples of the polycyclic compound formed by condensation of rings selected from Group A further encompass a polycyclic compound including an oxygen-containing ring, such as xanthene, in which a pyrane ring and benzene rings are ortho-fused, and dibenzofuran, in which a furane ring and benzene rings are ortho-fused.

The polycyclic compounds composed of the rings selected from Group A, which rings are formed solely from carbons (e.g. polycyclic hydrocarbon compounds) are preferred. Among the polycyclic compounds of the present invention polycyclic aromatic compound(s) (e.g. a fused polycyclic compound composed of benzene rings) is more preferred.

Still more preferable examples of the polycyclic compound encompass polycyclic compounds composed of 2 to 4 rings such as anthracene, phenanthrene, pyrene, tetracene, biphenyl, azulene, naphthalene, and such polycyclic compounds substituted with a substituent selected from Group B.

An amount of the polycyclic compound or the substituted polycyclic compound of the present invention to be added is generally in a range of 0.0001 mmol/kg to 100 mmol/kg per unit weight of solvent (i.e. unit weight of water, an organic solvent, or a mixture thereof), and preferably in a range of 0.001 mmol/kg to 1 mmol/kg.

Examples of the noble metal catalyst usable in the present invention encompass catalysts comprising palladium, platinum, ruthenium, gold, rhodium, or iridium; among the above noble metals, palladium is preferable. Such noble metals are usable in the form of metal, oxide, hydroxide, acetyl acetonato salt, carbonyl salt, and the like.

Preferable examples of the palladium catalyst encompass metal palladium, palladium oxide, palladium hydroxide, and palladium acetyl acetonato. Such palladium catalyst may be used in combination with a noble metal other than palladium such as platinum, gold, rhodium, iridium, or osmium, by mixing with palladium; among the above additive metals, platinum is preferable.

The noble metal which is supported on a carrier is generally used. The noble metal can be supported on a titanosilicate, or a carrier other than titanosilicates such as (i) an oxide such as silica, alumina, titania, zirconia, and niobia, (ii) niobic acid, (iii) zirconic acid, (iv) tungstic acid, (v) titanic acid, (vi) carbon, and (vii) a mixture of these. In cases where the carrier other than titanosilicates carries a noble metal, the carrier may be mixed with a titanosilicate, so that the mixture thereof is used as the catalyst. Among the carriers other than titanosilicates, carbon and niobic acid are preferable.

A method for supporting a noble metal, e.g. metal palladium, on a carrier is carried out as follows; a noble metal compound (such as palladium chloride or tetraammine palladium chloride) as a noble metal source is supported on a carrier by such a method as impregnation method, and then reduced in a liquid phase or in a gas phase generally at temperatures of 0° C. to 500° C. by a reducing agent such as hydrogen.

Examples of the titanosilicate described herein encompass a crystalline titanosilicate, layered titanosilicate, and mesoporous titanosilicate.

The titanosilicate usually has a composition represented by Formula (2) below:

$$xTiO_2 \cdot (1-x)SiO_2 \qquad \text{Formula (2)}$$

where x is generally in a range of 0.0001 to 0.5, and preferably in a range of 0.01 to 0.2.

Generally, Ti of the titanosilicate is incorporated into the $SiO_2$ framework, where part of Si is substituted by Ti. The inclusion of Ti in the $SiO_2$ framework can be easily confirmed by ultraviolet visible absorption spectrum analysis, titanium K-shell XAFS analysis, or the like.

Examples of the titanosilicate encompass (i) a crystalline titanosilicate having a pore composed of 10-membered oxygen ring such as TS-1 (e.g. Journal of Catalysis 130, 1-8, (1991)) and TS-2 (e.g. Applied Catalysis 58, L1-L4, (1991)), (ii) a crystalline titanosilicate having a pore composed of 12 or more-membered oxygen ring such as Ti-Beta (e.g. Journal of Catalysis 199, 41-47, (2001)), Ti-ZSM-12 (e.g. Zeolites 15, 236-242, (1995)), TAPSO-5 (e.g. Zeolites 15, 228-235, (1995)), Ti-MOR (e.g. The Journal of Physical Chemistry B 102, 9297-9303 (1998)), Ti-ITQ-7 (e.g. Chemical Communications 761-762, (2000)), Ti-UTD-1 (e.g. Zeolites 15, 519-525, (1995)), and Ti-MWW (e.g. Chemistry Letters 774-775, (2000)), (iii) a layered titanosilicate having a pore composed of 12 or more-membered oxygen ring such as a Ti-MWW precursor (e.g. Japanese Unexamined Patent Application Publication No. 262164/2005 (Tokukai 2005-262164), which is an equivalent of WO2005/090323), and (iv) a mesoporous titanosilicate such as Ti-MCM-41 (e.g. Microporous Materials 10, 259-271, (1997)), Ti-MCM-48 (e.g. Chemical Communications 145-146, (1996)), and Ti-SBA-15 (e.g. Chemistry of Materials 14, 1657-1664, (2002)). Among the above, Ti-MWW and the Ti-MWW precursor are preferable; the more preferable is Ti-MWW.

The titanosilicate may be silylated titanosilicate obtained by silylation of a titanosilicate by a silylating agent such as 1,1,1,3,3,3-hexamethyldisilazane, for example.

A liquid phase in which the reaction takes place is generally a mixture of solvents containing water and an organic solvent. Examples of such an organic solvent encompass various organic compounds such as an alcohol, a ketone compound, an ether compound, an ester compound, a nitrile compound, a hydrocarbon, and a halogenated hydrocarbon. A suitable organic solvent varies depending on the catalyst to be used; for example, a nitrile compound is preferably used in combination with the titanosilicate having a pore composed of 12 or more-membered oxygen ring such as Ti-MWW. An example of the preferable nitrile compound is acetonitrile. In cases where the titanosilicate having a pore composed of 10-membered oxygen ring such as TS-1 is used, an example of a preferable organic solvent is methanol. Generally, a ratio of water to the organic solvent is in a range from (i) 90:10 to (ii) 0.01:99.99 by weight, and preferably in a range from (i) 50:50 to (ii) 0.1:99.9. When the ratio of water is too high, sometimes, propylene oxide is apt to react with water, which causes deterioration due to ring opening, resulting in lowering the propylene oxide formation activity. To the contrary, when the ratio of the organic solvent is too high, recovery costs of the solvent becomes high.

In the present invention, a salt of ammonium, alkylammonium, or alkyl aryl ammonium may be charged into a reaction solvent with titanosilicate, the noble metal catalyst, and the substituted or unsubstituted polycyclic compound of the present invention. This effectively prevents decrease in catalytic activity and enhances it, and improves hydrogen use efficiency. The salt of ammonium, alkylammonium, or alkylaryl ammonium is added in an amount generally in a range from 0.001 mmol/kg to 100 mmol/kg per unit weight of solvent (i.e., in case of the mixture of water and organic solvent, the total weight thereof).

Ammonium may be added in the form of sulfate or hydrogen sulfate thereof, for example. Furthermore, ammonium may be added in the form of an inorganic salt thereof such as hydrogencarbonate, phosphate, hydrogen phosphate, dihydrogenphosphate, hydrogenpyrophosphate, pyrophosphate, a halide salt, or nitrate, or an organic acid (e.g. carboxylate) salts such as acetate.

The pH of the solution varies depending on the kind and/or amount of ammonium, alkylammonium, or alkylaryl ammonium to be added. However, an excessively high pH may decrease the activity of the propylene oxide production. Conversely, an excessively low pH may increase the amount of a propane byproduct and/or decrease the activity of propylene oxide production, which would result in decrease of a selectivity for propylene oxide. To prevent these, the amount of an additive may be controlled and/or a buffer may be added. The pH is generally adjusted in a range from 3 to 10.

Examples of reaction methods applicable to the present invention encompass a fixed-bed flow reaction and a slurry-bed flow reaction.

A partial pressure ratio of oxygen to hydrogen supplied to the reactor is generally in a range from (i) 1 to 50 to (ii) 50 to 1; and preferably in a range from (i) 1 to 2 to (ii) 10 to 1. Since the oxygen level should be out of an explosive range, an excessively high partial pressure ratio of oxygen to hydrogen, which means a low partial pressure of hydrogen, may lower a reaction rate. An excessively low partial pressure ratio of oxygen to hydrogen may result in an increased amount of the propane byproduct. The oxygen gas and hydrogen gas for use in the reaction may be diluted with a dilution gas. Examples of such a dilution gas encompass nitrogen gas, argon gas, carbon dioxide gas, methane gas, ethane gas, and propane gas. The concentration of dilution gas is not particularly limited; however, for the sake of safety, the reaction is preferably carried out by diluting oxygen or hydrogen to the range outside the explosive range.

Examples of an oxygen source encompass oxygen gas and air. Such oxygen gas may be produced by a pressure swing adsorption process, which is inexpensive. If necessary, a highly purified oxygen gas produced by a low temperature separation process or the like may be used.

The reaction is taken place at a reaction temperature generally in a range of 0° C. to 150° C., and preferably in a range of 40° C. to 90° C.

An excessively low reaction temperature decreases the reaction rate; and an excessively high reaction temperature increases an amount of a byproduct generated by side reaction.

The reaction is not particularly limited in terms of its reaction pressure. Generally, the reaction pressure is in a range of 0.1 MPa to 20 MPa by gauge pressure. Preferably the reaction pressure is in a range of 1 MPa to 10 MPa by gauge pressure. An excessively low reaction pressure results in insufficient dissolution of the source gas into the reaction solvent, thereby leading to a poor reaction rate. Conversely, an excessively high reaction pressure requires high costs of equipment used for reaction.

After the reaction, a resultant liquid phase or gas phase is withdrawn from the reactor, and then subjected to distillation separation to obtain the desired material.

EXAMPLES

The following examples explain the present invention. Yet, it should be noted that the present invention is not limited to such examples.

Example 1

A titanosilicate, Ti-MWW having a titanium content of 1.8 wt % according to an ICP emission spectrochemical analysis was prepared in accordance with the method described in Chemistry Letters 774-775 (2000). Specifically, 0.133 g of Ti-MWW powder was treated, at room temperature for 1 hour, with approximately 80 cc of a solution of water and acetonitrile (water:acetonitrile=20:80 by weight ratio) and containing 0.1 wt % hydrogen peroxide, and subsequently washed with 100 ml water before reaction. A noble metal catalyst used herein was 1 wt % palladium/activated carbon, prepared as follows, was used as. To a 300 ml aqueous solution containing 0.30 mmol of palladium tetraammine chloride prepared in a 500-ml eggplant-shaped flask were added 3 g of commercially available activated carbon powder (pore volume: 1.57 cc/g, manufactured by Wako Pure Chemical Industries, Ltd.) and then stirred for 8 hours. Then, the water was removed by a rotary evaporator, and palladium tetraammine chloride was impregnated on the activated carbon to make palladium tetraammine chloride supported on the activated carbon. Further, the resultant was dried in a vacuum at 50° C. for 12 hours to obtain a catalyst precursor powder. The catalyst precursor powder thus obtained was thereafter calcined at 300° C. under nitrogen atmosphere for 6 hours to obtain a palladium/activated carbon catalyst.

A 0.5-liter autoclave having a Teflon (registered trademark) inner vessel was used as a reactor. Reaction was carried out continuously at 60° C. under a pressure of 0.8 MPa (gauge pressure) with a residence time of 90 minutes by feeding a source gas containing propylene/oxygen/hydrogen/nitrogen at a ratio of 4/4/10/82 at 20 l/h and a solution of water and acetonitrile (20/80 wt ratio) containing 0.7 mmol/kg of anthracene at 108 ml/h was withdrawn through filter to separate a liquid phase from the reaction mixture. During the continuous reaction, 131 g of a reaction solvent, 0.133 g of Ti-MWW, and 0.03 g of palladium-activated carbon were retained in the reaction mixture in the reactor. A liquid phase and gas phase withdrawn after 5 hours from the start of the reaction were analyzed with gas chromatography. The analysis showed that the production activity of propylene oxide was 32.9 mmol-PO/g-Ti-MWW·h per unit weight of Ti-MWW. The selectivity based on propylene was 83%, while a selectivity based on hydrogen (mol of propylene oxide generated/mol of hydrogen consumed) was 25%.

Example 2

An experiment was carried out in a similar manner as in Example 1, except that an aqueous solution of acetonitrile, which contained water and acetonitrile at a weight ratio of 20 to 80 and containing 0.7 mmol/kg of xanthene was used, in place of the aqueous solution containing water and acetonitrile at the weight ratio of 20 to 80 and 0.7 mmol/kg of anthracene. The production activity of propylene oxide was 32.9 mmol-PO/g-Ti-MWW·h per unit weight of Ti-MWW. The selectivity based on propylene was 39%, while the selectivity based on hydrogen (mol of propylene oxide generated/mol of hydrogen consumed) was 17%.

Example 3

An experiment was carried out in a similar manner as in Example 1, except that an aqueous solution of acetonitrile, containing water and acetonitrile at a weight ratio of 20 to 80 and containing 0.7 mmol/kg of biphenyl was used, in place of the aqueous solution containing water and acetonitrile at the weight ratio of 20 to 80 and 0.7 mmol/kg of anthracene. The production activity of propylene oxide was 35.7 mmol-PO/g-Ti-MWW·h per unit weight of Ti-MWW. The selectivity based on propylene was 74%, while the selectivity based on hydrogen (mol of propylene oxide generated/mol of hydrogen consumed) was 24%.

Example 4

An experiment was carried out in a similar manner as in Example 1, except that an aqueous solution of acetonitrile, containing water and acetonitrile at a weight ratio of 20 to 80 and containing 0.07 mmol/kg of diphenyl ether was used, in place of the aqueous solution containing water and acetonitrile at the weight ratio of 20 to 80 and 0.7 mmol/kg of anthracene. The production activity of propylene oxide was 31.4 mmol-PO/g-Ti-MWW·h per unit weight of Ti-MWW. The selectivity based on propylene was 35%, while the selectivity based on for hydrogen (mol of propylene oxide generated/mol of hydrogen consumed) was 13%.

Example 5

An experiment was carried out in a similar manner as in Example 1, except that an aqueous solution of acetonitrile, containing water and acetonitrile at a weight ratio of 20 to 80 and containing 0.007 mmol/kg of tetracene was used, in place of the aqueous solution containing water and acetonitrile at the weight ratio of 20 to 80 and 0.7 mmol/kg of anthracene.

Example 6

An experiment was carried out in a similar manner as in Example 1, except that an aqueous solution of acetonitrile, containing water and acetonitrile at a weight ratio of 20 to 80 and containing 0.7 mmol/kg of 9-methylanthracene was used, in place of the aqueous solution containing water and acetonitrile at the weight ratio of 20 to 80 and 0.7 mmol/kg of anthracene.

Comparative Example 1

An experiment was carried out in a similar manner as in Example 1, except that an aqueous solution of acetonitrile, containing water and acetonitrile at a weight ratio of 20 to 80 and containing 0.7 mmol/kg of benzothiophene was used, in place of the aqueous solution containing water and acetonitrile at the weight ratio of 20 to 80 and 0.7 mmol/kg of anthracene.

Comparative Example 2

An experiment was carried out in a similar manner as in Example 1, except that an aqueous solution of acetonitrile, containing water and acetonitrile at a weight ratio of 20 to 80 and containing 0.7 mmol/kg of thioxanthene was used, in place of the aqueous solution containing water and acetonitrile at the weight ratio of 20 to 80 and 0.7 mmol/kg of anthracene.

Results of Examples 5 and 6, and Comparative Examples 1 and 2 are shown in Table 1 below.

In Table 1, "Concentration" refers to a concentration of the additive in the solution (mmol·kg$^{-}$·solution); "Activity" refers to production activity of propylene oxide per unit weight of Ti-MWW (mmol-PO·g$^{-1}$-Ti-MWW·h$^{-1}$); "PO" refers to propylene oxide; "Selectivity of PO based on propylene" refers to mole amount of PO generated/(mole amount of PO generated+mole amount of propylene glycol generated+mole amount of propane generated); "Selectivity of propane based on propylene" refers to mole amount of propane generated/(mole amount of PO generated+mole amount of propylene glycol generated+mole amount of propane generated); "Selectivity of propane based on hydrogen" refers to mole amount of PO generated/mole amount of hydrogen consumed.

Example 7

An experiment was carried out in a similar manner as in Example 1, except that an aqueous solution of acetonitrile, containing water and acetonitrile at a weight ratio of 20 to 80 and containing 0.7 mmol/kg of anthracene and 0.7 mmol/kg of ammonium dihydrogenphosphate was used, in place of the aqueous solution containing water and acetonitrile at the weight ratio of 20 to 80 and 0.7 mmol/kg of anthracene.

Example 8

An experiment was carried out in a similar manner as in Example 1, except that an aqueous solution of acetonitrile, containing water and acetonitrile at a weight ratio of 20 to 80 and containing 0.7 mmol/kg of naphthalene and 0.7 mmol/kg of ammonium dihydrogenphosphate was used, in place of the aqueous solution containing water and acetonitrile at the weight ratio of 20 to 80 and 0.7 mmol/kg of anthracene.

Example 9

An experiment was carried out in a similar manner as in Example 1, except that an aqueous solution of acetonitrile, containing water and acetonitrile at a weight ratio of 20 to 80 and containing 0.007 mmol/kg of tetracene and 0.7 mmol/kg of ammonium dihydrogenphosphate was used, in place of the aqueous solution containing water and acetonitrile at the weight ratio of 20 to 80 and 0.7 mmol/kg of anthracene.

Example 10

An experiment was carried out in a similar manner as in Example 1, except that an aqueous solution of acetonitrile, containing water and acetonitrile at a weight ratio of 20 to 80 and containing 0.07 mmol/kg of pyrene and 0.7 mmol/kg of ammonium dihydrogenphosphate was used, in place of the aqueous solution containing water and acetonitrile at the weight ratio of 20 to 80 and 0.7 mmol/kg of anthracene.

Results of Examples 7, 8, 9, and 10 are shown in Table 2 below.

TABLE 1

| Number | Additive | Concentration | Activity | Selectivity of PO based on propylene % | Selectivity of propane based on propylene % | Selectivity of propane based on hydrogen % |
|---|---|---|---|---|---|---|
| Example 5 | tetracene | 0.007 | 30.5 | 77 | 22 | 18 |
| Example 6 | 9-methylanthracene | 0.7 | 30.1 | 79 | 19 | 23 |
| Comparative Example 1 | benzothiophene | 0.7 | 1.1 | 73 | 15 | 14 |
| Comparative Example 2 | thioxanthene | 0.7 | 20.0 | 61 | 37 | 30 |

TABLE 2

| Number | Additive | Concentration | Activity | Selectivity of PO based on propylene % | Selectivity of propane based on propylene % | Selectivity of propane based on hydrogen % |
| --- | --- | --- | --- | --- | --- | --- |
| Example 7 | anthracene | 0.7 | 33.5 | 87 | 12 | 39 |
| Example 8 | naphthalene | 0.7 | 32.2 | 66 | 33 | 36 |
| Example 9 | tetracene | 0.007 | 41.7 | 78 | 21 | 29 |
| Example 10 | pyrene | 0.07 | 37.6 | 70 | 29 | 38 |

In Table 2, "Concentration" refers to a concentration of the additive in the solution (mmol·kg⁻·solution); "Activity" refers to production activity of propylene oxide per unit weight of Ti-MWW (mmol-PO·g$^{-1}$-Ti-MWW·$^{-1}$); "PO" refers to propylene oxide; "Selectivity of PO based on propylene" refers to mole amount of PO generated/(mole amount of PO generated+mole amount of propylene glycol generated+mole amount of propane generated); "Selectivity of propane based on propylene" refers to mole amount of propane generated/(mole amount of PO generated+mole amount of propylene glycol generated+mole amount of propane generated); "Selectivity of propane based on hydrogen" refers to mole amount of PO generated/mole amount of hydrogen consumed.

Reference Example

An experiment was carried out in a similar manner as in Example 1, except that an aqueous solution of acetonitrile, containing water and acetonitrile at a weight ratio of 20 to 80 and containing no anthracene was used, in place of the aqueous solution containing water and acetonitrile at the weight ratio of 20 to 80 and 0.7 mmol/kg of anthracene. The production activity of propylene oxide was 30.9 mmol-PO/g-Ti-MWW·h per unit weight of Ti-MWW. The selectivity based on propylene was 27%, while the selectivity based on for hydrogen (mol of propylene oxide generated/mol of hydrogen consumed) was 13%.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The invention claimed is:

1. A method for producing propylene oxide, which comprises:
    reacting propylene, oxygen, and hydrogen in the presence of a noble metal catalyst and a titanosilicate catalyst in a liquid phase containing
    a polycyclic aromatic compound, which is unsubstituted or substituted with at least one substituent selected from Group B below,
    wherein the polycyclic aromatic compound is composed of 2 to 4 identical or different ring compounds selected from Group A below and the ring compounds are fused, directly bonded, or bonded by a linkage group selected from the group consisting of an oxygen atom, carbon chain, and a group composed of oxygen atom(s) and a carbon chain,
    provided that said polycyclic aromatic compound is not a polycyclic aromatic compound having hydroxy groups or oxo groups at para or ortho positions;
    wherein Group A consists of benzene, cyclopentadiene, cycloheptatriene, furane, pyrane, cyclopentene, cyclopentane, cyclohexane, cyclohexene, cyclohexadiene, cyclohcptanc, cycloheptene, and cycloheptadiene; and
    wherein Group B consists of halogen atom, alkyl group, alkenyl group, alkoxy group, hydroxyalkyl group, acyl group, oxo group, hydroxy group, and cyano group.

2. The method for producing propylene oxide according to claim 1, wherein the polycyclic aromatic compound is a fused polycyclic compound.

3. The method for producing propylene oxide according to claim 1, wherein the noble metal catalyst is a palladium catalyst.

4. The method for producing propylene oxide according to claim 1, wherein the titanosilicate catalyst is Ti-MWW or a Ti-MWW precursor.

5. The method for producing propylene oxide according to claim 1, wherein a solvent comprising acetonitrile is used.

6. The method for producing propylene oxide according to claim 1, wherein the polycyclic aromatic compound is pentalene, naphthalene, heptalene, indane, indene, azulene, anthracene, phenanthrene, phenalene, dihydroanthracene, indacene, fluorene, dibenzosuberane, tetracene, pyrene, triphenylene, chrysene, tetraphene, fluoracene, 1H-cyclopenta[a]phenanthrene, or dibenzo[c,g]phenanthrene.

7. The method for producing propylene oxide according to claim 1, wherein the polycyclic aromatic compound is 9-acetylanthracene, anthracene-9-methanol, 9-bromoanthracene, 2-(t-butyl)anthracene, 9,10-diethoxyanthracene, 9,10-dimethylanthracene, 9-methylanthracene, 9-vinylanthracene, dihydroanthracene, or anthrone.

8. The method for producing propylene oxide according to claim 1, wherein the polycyclic aromatic compound is 1H,1'H-2,2'-spirobi[naphthalene], biphenyl, cyclohexylbenzene, 1-phenyl-1-cyclohexene, 1,4-dicyclohexylbenzene, diphenylmethane, bibenzyl, triphenylmethane, tetraphenylmethane, or diphenyl ether.

9. The method for producing propylene oxide according to claim 1, wherein the polycyclic aromatic compound is xanthene or dibenzofuran.

10. The method for producing propylene oxide according to claim 1, wherein the polycyclic aromatic compound is anthracene, phenanthrene, pyrene, tetracene, azulene, or naphthalene.

* * * * *